United States Patent [19]
Bencini

[11] Patent Number: 5,401,248
[45] Date of Patent: Mar. 28, 1995

[54] SEAL FOR TROCAR ASSEMBLY

[75] Inventor: Robert F. Bencini, Sunnyvale, Calif.

[73] Assignee: Ethicon Endo-Surgery, Cincinnati, Ohio

[21] Appl. No.: 199,902

[22] Filed: Feb. 22, 1994

[51] Int. Cl.6 .................................. A61M 5/178
[52] U.S. Cl. .................... 604/167; 251/149.3; 604/169; 604/264
[58] Field of Search ............. 604/30, 33–34, 604/167, 169, 246, 247, 249, 264; 251/4, 149.1, 149.3; 137/843, 853

[56] References Cited

U.S. PATENT DOCUMENTS

| | | | |
|---|---|---|---|
| 2,592,569 | 4/1952 | Henderson | 251/4 X |
| 2,800,905 | 7/1957 | Simmons et al. | 251/4 X |
| 4,143,853 | 3/1979 | Abramson | 251/149.1 |
| 4,424,833 | 1/1984 | Spector et al. | 137/849 |
| 4,475,548 | 10/1984 | Muto | 128/207.14 |
| 4,809,679 | 3/1989 | Shimonaka et al. | 128/4 |
| 5,071,411 | 12/1991 | Hillstead | 604/246 |
| 5,073,168 | 12/1991 | Danforth | 604/167 |
| 5,141,498 | 8/1992 | Christian | 604/167 |
| 5,158,553 | 10/1992 | Berry et al. | 604/248 |
| 5,205,325 | 4/1993 | Piper | 137/844 |
| 5,242,412 | 9/1993 | Blake | 604/167 |

Primary Examiner—Corrine Maglione

[57] ABSTRACT

An elastomeric seal for a trocar assembly is disclosed. The seal can be used in a trocar device to seal against loss of gas pressure during a laparoscopic surgical procedure when a surgical instrument is inserted therethrough as well as when no instrument is inserted. The preferred one piece seal is cylindrical and has first and second collapsed sections defining generally a curved slit. The elastomeric seal is preferably composed of a silicone rubber. The seal has the advantages of simplicity of manufacture and assembly and the ability to provide an adequate seal against the surface of any surgical instrument inserted through it. Also, the improved seal will require a small amount of force to insert instruments and will resist eversion when instruments are withdrawn.

5 Claims, 6 Drawing Sheets

SEAL FOR TROCAR ASSEMBLY

BACKGROUND OF THE INVENTION

This invention relates generally to a trocar seal which prevents loss of gas pressure when an instrument is inserted through, or withdrawn from, the seal. More specifically, it relates to a flexible, elastomeric seal especially suited for use with surgical instruments necessary for numerous laparoscopic procedures.

Sealing devices for trocar assemblies are an important aspect of the design of instruments used in laparoscopic surgical procedures. A laparoscopic surgical procedure utilizes several small puncture openings, mainly in the abdominal wall, to allow insertion of specialized surgical instruments instead of one large incision in a traditional open surgical procedure. The laparoscopic procedure is becoming widely accepted because of its many advantages such as: less trauma to the patient, shorter recovery time, reduced adhesions, and less post operative pain. The laparoscopic surgical technique requires inflation of the abdominal cavity to lift the abdominal wall from the internal organs to create working space for the surgeon and to introduce light generating and optical viewing instruments.

During the laparoscopic surgical procedure, the internal gas pressure must be maintained in order to successfully complete the procedure. In order to maintain the internal gas pressure while instruments are passed into and out of the openings in the abdominal cavity, sealing devices are required for both the instruments and for the trocar assemblies used to make and maintain the small openings. In a trocar assembly, the obturator punctures the pressurized abdomen. The obturator generally slides within the cannula of the trocar assembly, which is the hollow tube portion of the trocar which remains in the abdominal wall after puncturing.

During the laparoscopic procedure, it is desirable to seal the cannula from loss of internal gas pressure. The seal functions while the obturator pierces the abdominal wall, after the obturator is withdrawn, and while other instruments are inserted through the cannula. Additionally, it is desirable that the seal produce a small amount of resistance to the insertion force by surgical instruments passing through the trocar cannula. Furthermore, it is desirable that the seal maintain gas pressure in the abdominal cavity, despite numerous insertions and withdrawals of surgical instruments through the trocar cannula.

Current sealing devices for laparoscopic instruments are typified by numerous designs. For example, one design includes a spring loaded valve in combination with a sealing gasket to conform to the cross section of the surgical instrument inserted through the trocar cannula. This two part valve assembly performs adequately as a seal but may be more complex than truly desired. U.S. Pat. No. 5,141,498 shows at least three flexible leaflets, and U.S. Pat. No. 4,424,833 shows a sponge type seal with three connecting slits.

Multiple leaflet and multiple slit devices may seal well when a surgical instrument is not inserted through them but will tend to create gaps around inserted instruments having circular cross sections and will also tend to cause eversion of their sealing surfaces when the instruments are withdrawn. Eversion of the sealing surfaces is likely to cause gaps between the sealing surfaces resulting in gas leakage through the seal. U.S. Pat. No. 5,242,412 shows a duck bill valve design applied to a trocar device. This design provides a straight single slit to seal against a surgical instrument. U.S. Pat. Nos. 4,475,548; 4,809,679; and 4,143,853 show single slit designs also. A single slit seal is also subject to a lack of conforming to circular shapes and to eversion upon withdrawal of surgical instruments.

A study of these references indicates a need for a simpler one piece seal for use in trocars to seal against gas pressure during a laparoscopic surgical procedure. In addition, it is desirable to have a one piece assembly with a simple design which would not require an excessive force to insert an instrument through it and would resist eversion of the sealing edges once the surgical instrument is withdrawn.

SUMMARY OF THE INVENTION

According to the present invention, the object of providing and maintaining gas pressure during a laparoscopic surgical procedure is achieved using a one piece seal in a trocar assembly. One aspect of the invention comprises a flexible elastomeric seal in the shape of a cylindrical tube. The tube has cylindrical entrance and exit passageways, and a cylindrical exterior wall section communicating with these passageways. First and second collapsed seal wall sections are displayed between the entrance and exit passageways, and these sections converge adjacent the exterior wall section to define a generally curved sealing slit between the entrance and exit passageways. The curved sealing slit will conform to surgical instruments as they are inserted through the seal to prevent loss of gas pressure in the abdominal cavity. The flexible seal is preferably made from silicone rubber.

In another aspect of the invention, a trocar assembly is described incorporating the seal described above. The assembly comprises a handle housing having a cannula passage, a cannula attached to the handle housing for receiving an obturator therethrough, a seal as already described for self sealing when an obturator or other surgical instrument is inserted through, or withdrawn from the cannula, an obturator slidably received in the handle housing for insertion through the cannula, and an obturator handle attached to the obturator.

The elastomeric seal of this invention has the advantages of simplicity of manufacture and assembly, and the ability to provide an adequate seal against the surface of any surgical instrument inserted through it.

Also, this seal will require only a small amount of force to insert instruments, and will resist eversion of the seal walls when instruments are withdrawn. Once an instrument is withdrawn, the seal will close and resist gas leakage.

The flexible elastomeric seal of this invention is used to effectively seal surgical instruments such as trocars against loss of gas pressure when surgical instruments are inserted during laparoscopic procedures. Additionally, the seal can be used to seal around any other instruments or devices inserted through it for any reason.

DETAILED DESCRIPTION OF THE PREFERRED EMBODIMENT

Figure 1:
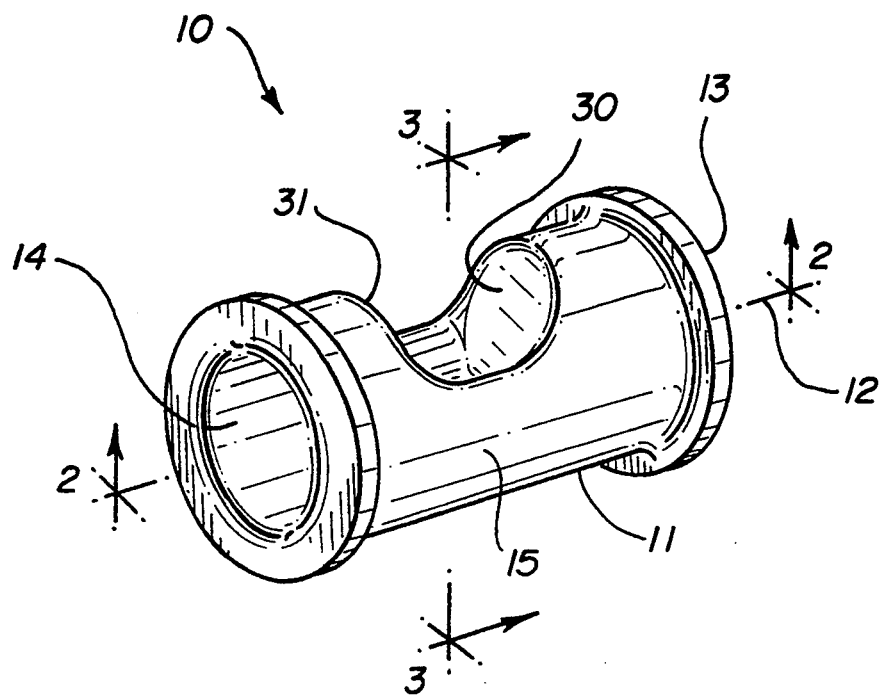
FIG. 1 is a perspective view of the flexible elastomeric seal.
Figure 2:
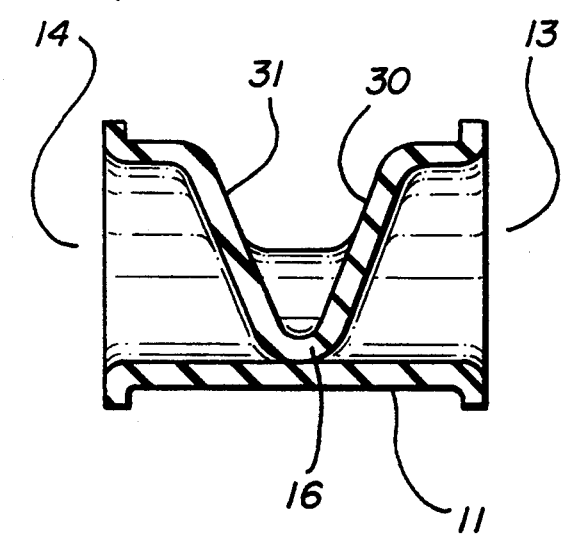
FIG. 2 is a cross-sectional view of the flexible elastomeric seal taken along lines 2—2 of FIG. 1.
Figure 3:
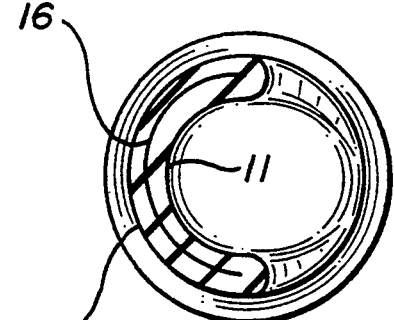
FIG. 3 is a cross-sectional view of the flexible elastomeric seal taken along lines 3—3 of FIG. 1.
Figure 4:
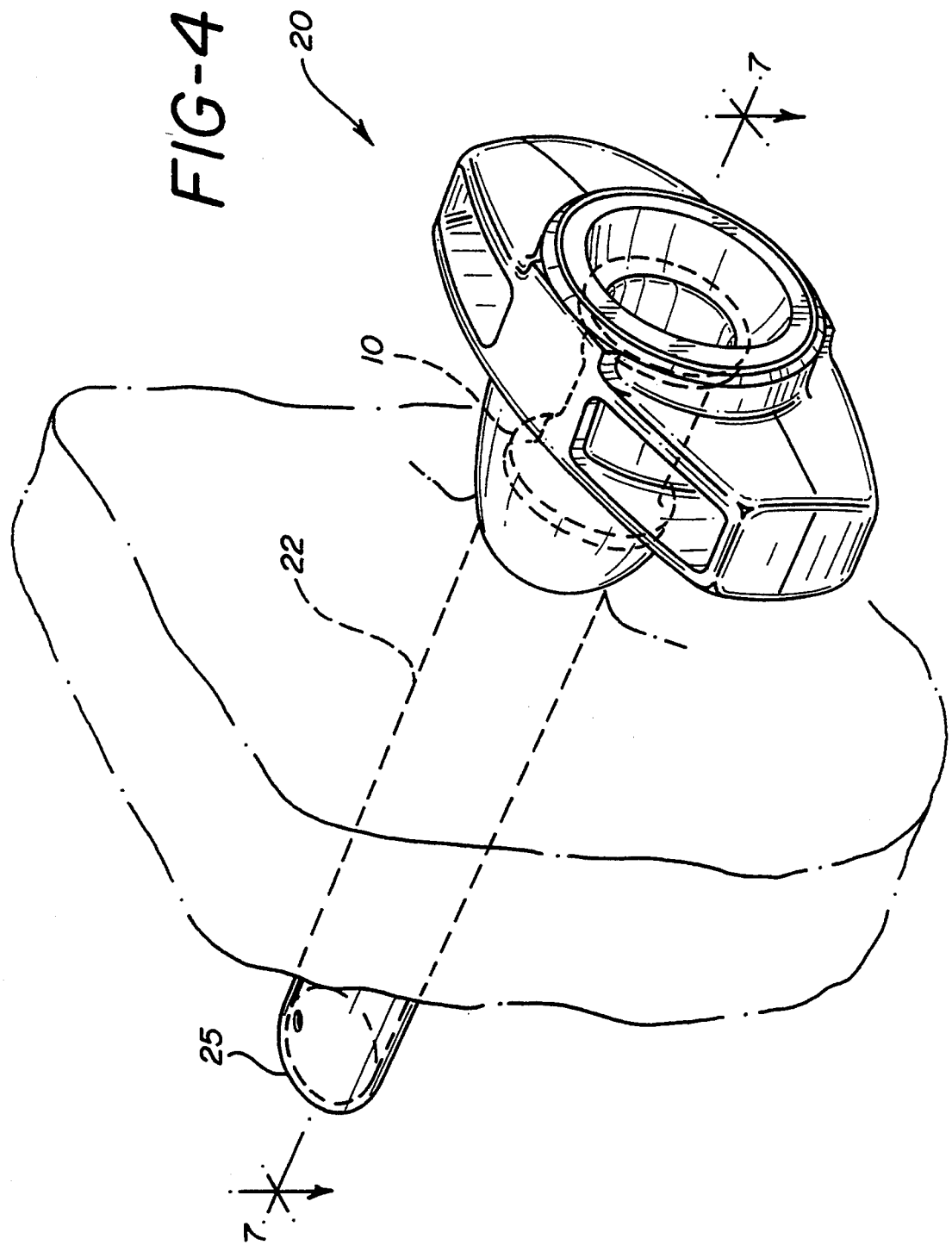
FIG. 4 is a perspective view of a trocar with the flexible elastomeric seal in place.

The flexible elastomeric seal and trocar assembly in which the seal is used are illustrated in FIGS. 1-8. The flexible elastomeric seal itself is shown in FIGS. 1-3 and its position and function in a trocar are shown in FIGS. 4-8.

Referring now to FIGS. 1-3, there is shown a perspective view of the flexible one-piece, elastomeric seal 10. The elastomeric seal 10 is shaped in the form of a cylindrical wall tube 11 centered on a longitudinal axis 12. This tube has a cylindrical entrance passageway 13, cylindrical exit passageway 14, and a cylindrical exterior wall section 15 communicating with these passageways.

In between the entrance and exit passageways, there is displayed first and second collapsed sealing wall sections, 30, 31, respectively. These sections converge in a manner to generally define a U-shaped curved sealing slit 16. This slit acts as a gas pressure seal when no surgical instrument is inserted through the seal 10, The slit 16 can also stretch to contact the surface of an inserted instrument to provide a seal around the instrument.

In the preferred embodiment, the sealing slit 16 is substantially equidistant between the entrance and exit passageways 13, 14. The preferred material of construction for seal 10 is silicone rubber.

Figure 5:
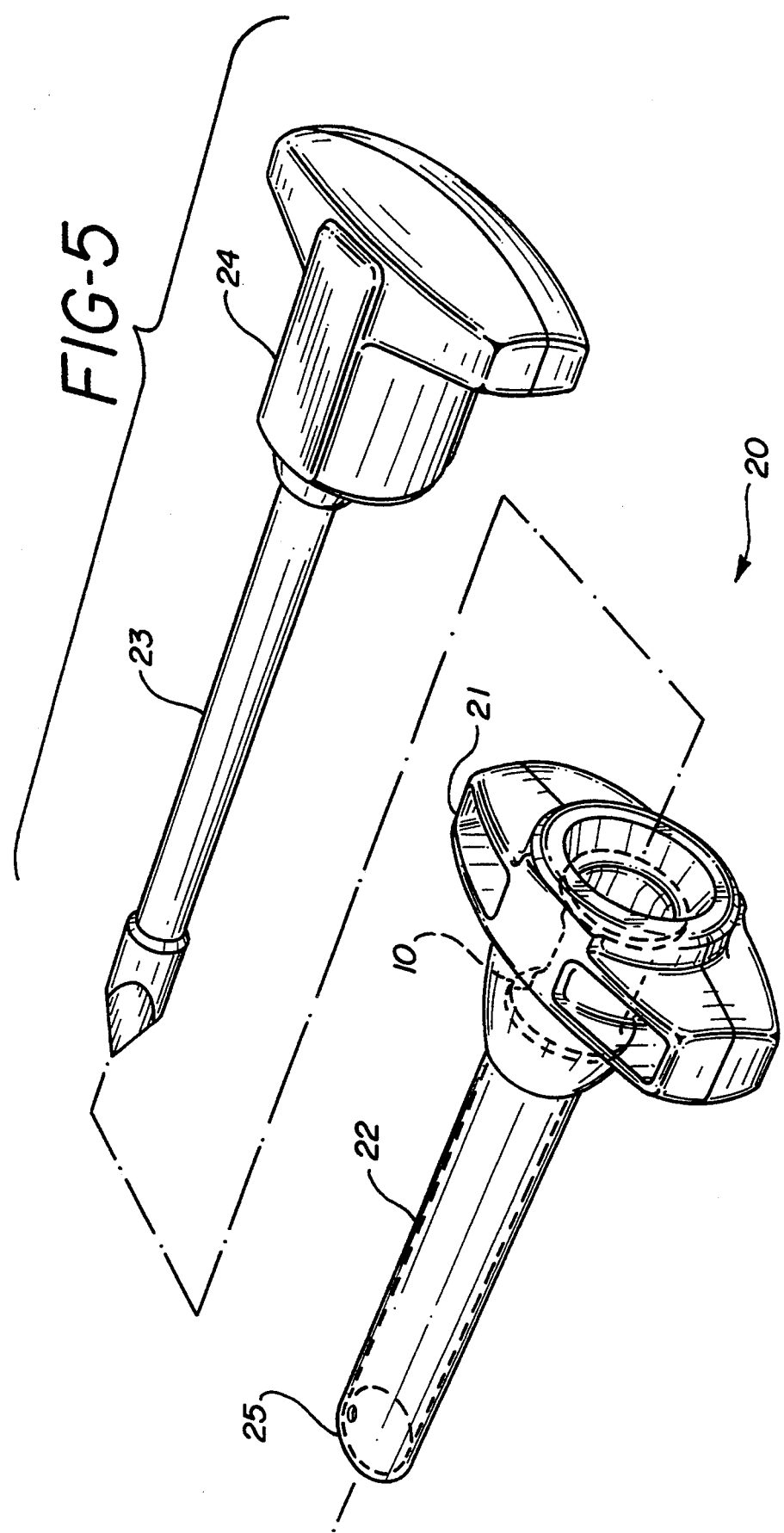
FIG. 5 is an exploded perspective view of a trocar with the flexible elastomeric seal in place.
Figure 6:
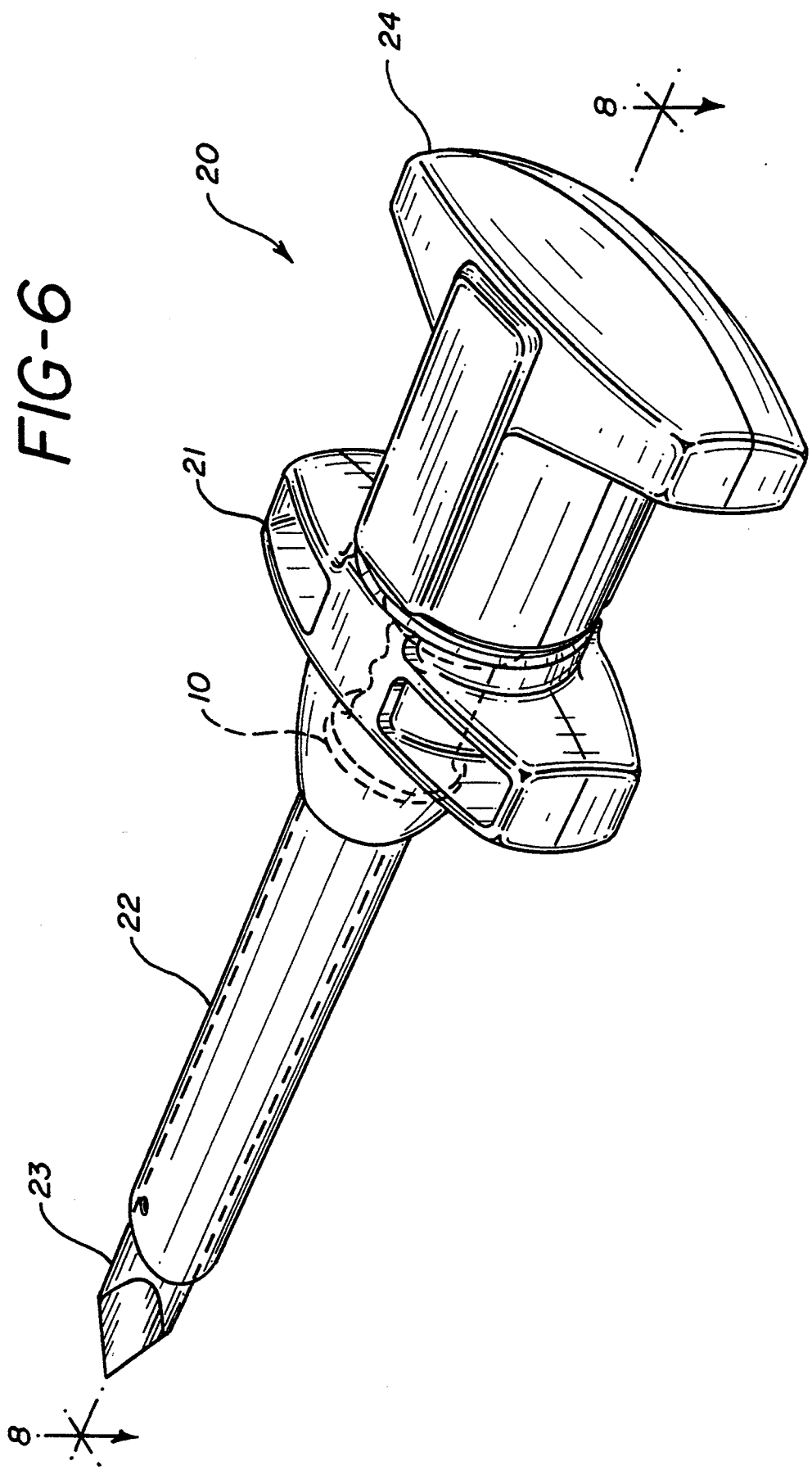
FIG. 6 is an assembled perspective view of a trocar with the flexible elastomeric seal in place.
Figure 7:
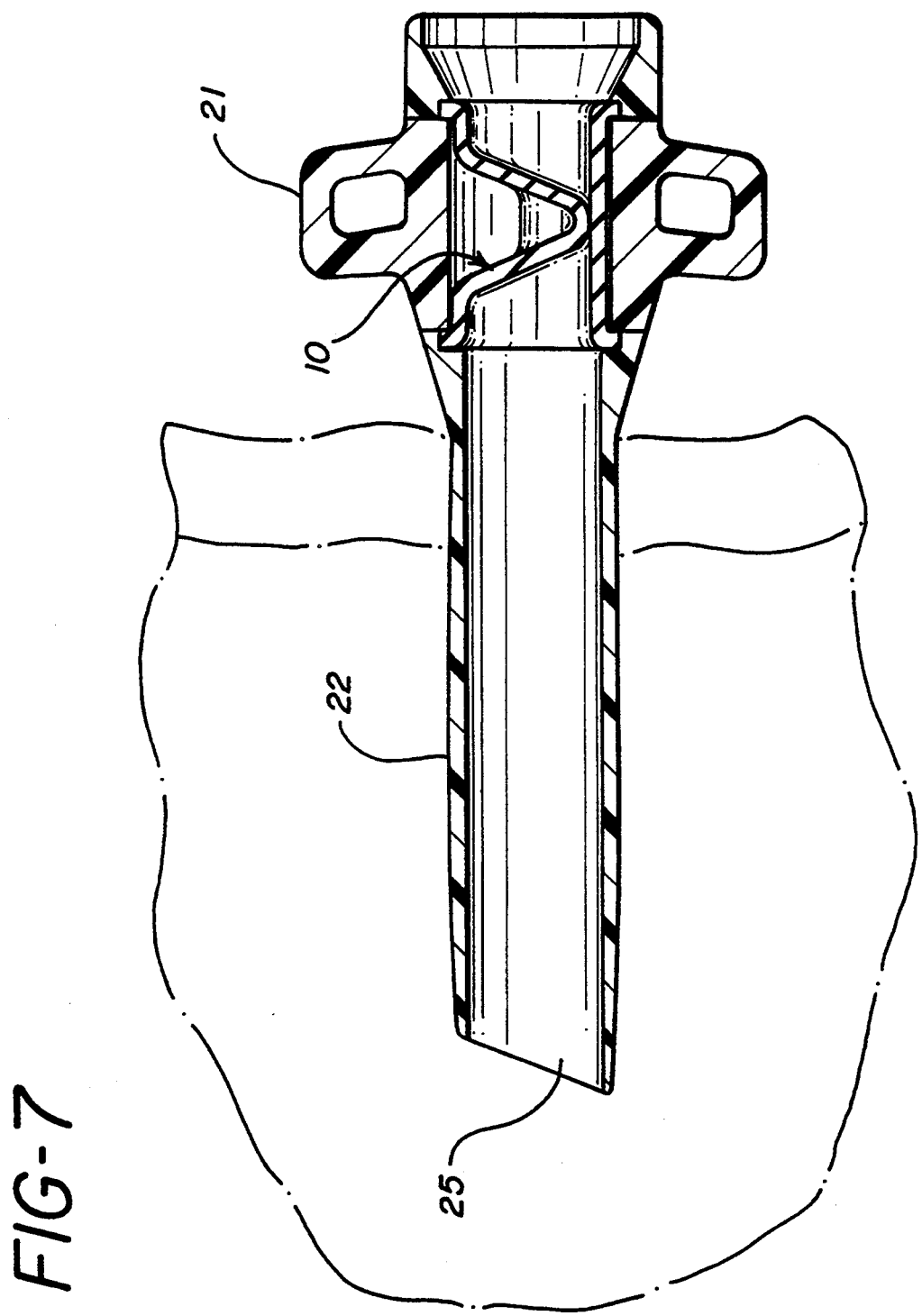
FIG. 7 is a cross-sectional view of a trocar with the flexible elastomeric seal in place taken along lines 4—4 of FIG. 4.
Figure 8:
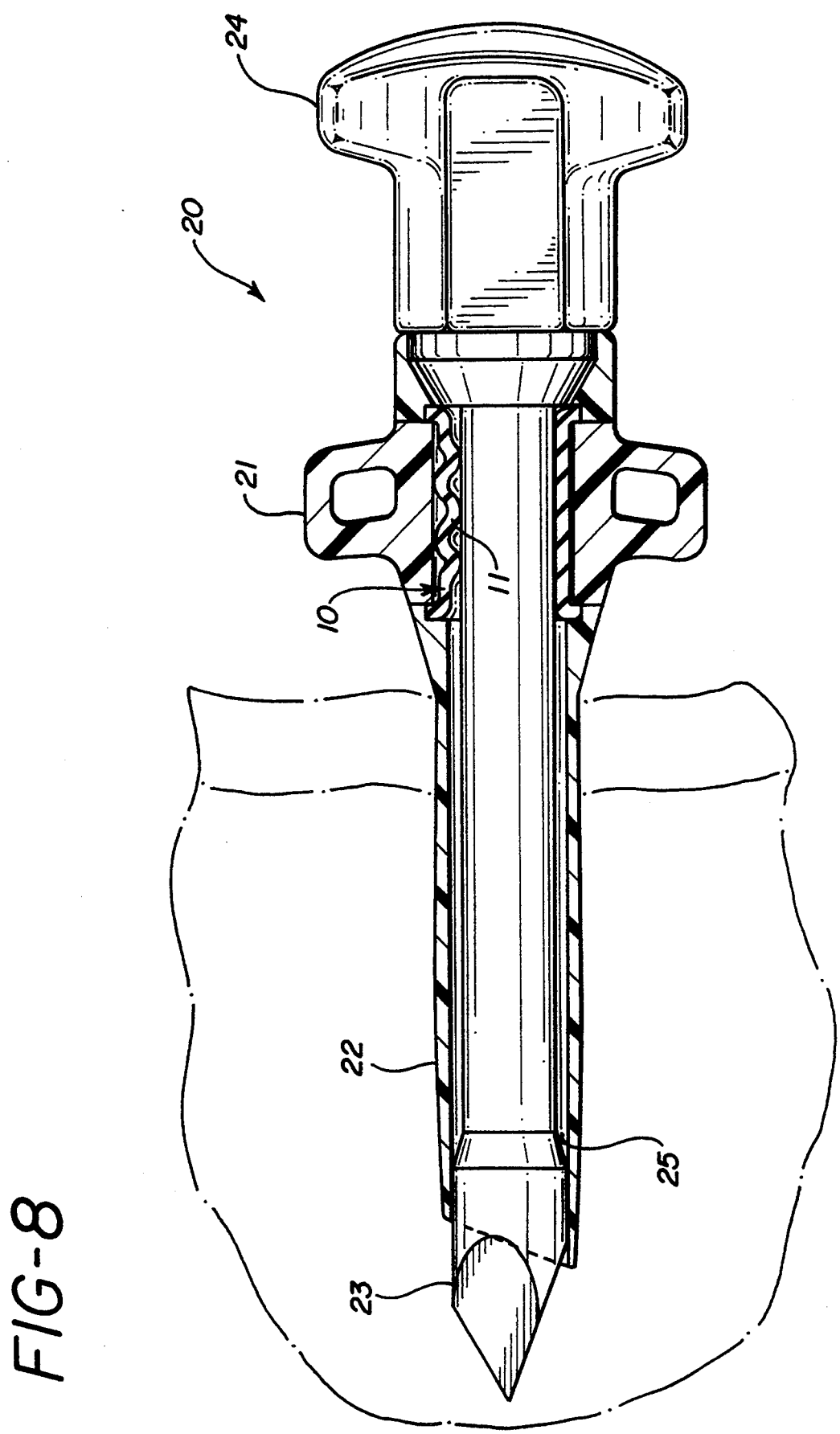
FIG. 8 is a cross-sectional view of an assembled trocar with the flexible elastomeric seal in place taken along lines 5—5 of FIG. 6.

The flexible elastomeric seal 10 is the sealing component of a trocar assembly 20 as shown in FIGS. 4-8. FIG. 5 shows the major components of a typical trocar assembly and FIGS. 6 and 8 show the assembled trocar. The typical components include: a handle housing 21, a cannula 22 attached to the handle housing 21, an obturator 23, and an attached obturator handle 24. The cannula 22 and handle housing 21 contain a cannula passage 25 for receiving the obturator 23 or other surgical instrument.

The flexible elastomeric seal 10 is restrained in the trocar handle housing 21. FIG. 7 shows a method of restraining the flexible elastomeric seal 10 in a trocar handle housing 21. Various means of restraint can be used. FIG. 7 also shows the seal when used to seal against loss of gas pressure with no instrument inserted. When a trocar obturator 23 or other surgical instrument is inserted, the seal 10 also seals against loss of gas pressure as shown in FIGS. 6 and 8. The FIG. 8, the seal 10 is shown in a sectional view with the sealing walls 11 opened by an inserted obturator 23. The sealing walls 11 conform to the shape of the instrument 23 inserted through them to cause the sealing of gas pressure.

This invention has been described with respect to its most preferred embodiment. However, the reader should realize that numerous additional embodiments are contemplated within the scope of this invention as it is defined by the appended claims.

What is claimed is:

1. A trocar assembly comprising:

a handle housing having a cannula passage, a cannula attached to said handle housing for receiving an obturator or other surgical instrument therethrough, a flexible elastomeric seal retained in said handle housing for sealing when said obturator or said other surgical instrument is inserted through said cannula or when said obturator or said other surgical instrument is withdrawn from said cannula, said seal adapted to have an instrument inserted into, or withdrawn from, said seal, said seal comprising a cylindrical tube having a cylindrical entrance passageway and a cylindrical exit passageway, a radially stationary cylindrical exterior wall section communicating with said entrance and exit passageways, first and second collapsed sealing wall sections extending from said cylindrical exterior wall section and displayed between said entrance and exit passageways, wherein said first and second sealing wall sections converge so as to define a generally curved sealing slit between said entrance and exit passageways, and said slit expands so as to form an opening therethrough for sealing engagement with said obturator or other surgical instrument in response to insertion of said obturator or said other surgical instrument through said slit, an obturator slidably received in said handle housing for insertion through said cannula, and an obturator handle attached to said obturator.

2. A seal as in claim 1 wherein said seal is one piece seal.

3. A seal as in claim 2 wherein said sealing slit is a generally U-shaped curve.

4. A seal as in claim 3 wherein said sealing slit is equidistant between said entrance and exit passageways.

5. A seal as in claim 4 wherein said seal is made from a silicone rubber.

* * * * *